US009993317B2

(12) United States Patent
Kottemann et al.

(10) Patent No.: US 9,993,317 B2
(45) Date of Patent: Jun. 12, 2018

(54) CLASS II MALOCCLUSION CORRECTION APPLIANCE FOR REMOVABLE ALIGNERS

(71) Applicant: KOTTEMANN ORTHODONTICS PLLC, Maple Grove, MN (US)

(72) Inventors: Kraig Jennings Kottemann, Mound, MN (US); Scott William Kottemann, Minneapolis, MN (US)

(73) Assignee: KOTTEMANN ORTHODONTICS PLLC, Maple Grove, MN (US)

( * ) Notice: Subject to any disclaimer, the term of this patent is extended or adjusted under 35 U.S.C. 154(b) by 0 days. days.

(21) Appl. No.: 14/848,054

(22) Filed: Sep. 8, 2015

(65) Prior Publication Data
US 2016/0067014 A1     Mar. 10, 2016

Related U.S. Application Data

(60) Provisional application No. 62/047,386, filed on Sep. 8, 2014.

(51) Int. Cl.
  *A61C 7/36* (2006.01)
(52) U.S. Cl.
  CPC ....................................... *A61C 7/36* (2013.01)
(58) Field of Classification Search
  CPC ................ A61C 7/36; A61C 7/08; A61C 7/10
  USPC .................................................. 433/6, 18, 19
  See application file for complete search history.

(56) References Cited

U.S. PATENT DOCUMENTS 3,690,003 A * 9/1972 Gerber ..................... A61C 7/12
                                                       433/18
3,798,773 A    3/1974  Northcutt
4,462,800 A    7/1984  Jones
4,708,646 A   11/1987  Jasper
5,352,116 A   10/1994  West
5,632,618 A    5/1997  Jensen
5,711,667 A    1/1998  Vogt
5,752,823 A    5/1998  Vogt
5,944,518 A    8/1999  Sabbagh (Continued)

FOREIGN PATENT DOCUMENTS

FR       2760631 A1     9/1998
KR     20050115152 A    12/2005

OTHER PUBLICATIONS http://irvinepdo.com/brace-appliances.html.
http://www.mkbraces.com/types-of-appliances.php.

*Primary Examiner* — Nicholas Lucchesi
(74) *Attorney, Agent, or Firm* — Schwabe Williamson & Wyatt, P.C.

(57) ABSTRACT

An orthodontic correction appliance may be directly connected to upper and lower removable orthodontic aligners to treat a Class II malocclusion. In some examples, the correction appliance has two elongated sections that are slidably connected to each other and allowed to move back and forth relative to each other. The ends of the two elongated sections can be attached to connectors extending from the removable aligners. In addition, the correction appliance can carry a biasing member that is connected to each of the two elongated sections of the appliance. The biasing member may bias the ends of the two elongated sections away from each other, providing a force to treat the Class II malocclusion while the patient is wearing the upper and lower removable orthodontic aligners.

27 Claims, 7 Drawing Sheets

(56) References Cited

U.S. PATENT DOCUMENTS

| | | | |
|---|---|---|---|
| 5,964,588 A * | 10/1999 | Cleary | A61C 7/36 433/18 |
| 6,027,340 A | 2/2000 | Chun | |
| 6,113,390 A | 9/2000 | Sirney et al. | |
| 6,162,051 A | 12/2000 | Brehm et al. | |
| 6,322,357 B1 | 11/2001 | Vogt | |
| 6,328,562 B1 | 12/2001 | Sirney et al. | |
| 6,547,560 B1 | 4/2003 | Vazquez | |
| 6,884,067 B2 | 4/2005 | Tuneberg | |
| 7,578,671 B2 | 8/2009 | Corcoran et al. | |
| 8,177,552 B1 | 5/2012 | Lawner et al. | |
| 8,348,664 B2 | 1/2013 | Sheikh et al. | |
| 9,180,034 B1 * | 11/2015 | Kapil | A63B 21/00 |
| 2002/0192617 A1 * | 12/2002 | Phan | A61C 7/00 433/6 |
| 2004/0219474 A1 * | 11/2004 | Cleary | A61C 7/36 433/19 |
| 2007/0190477 A1 * | 8/2007 | Sheikh | A61C 7/36 433/19 |
| 2009/0126742 A1 * | 5/2009 | Summer | A61F 5/566 128/848 |
| 2011/0129785 A1 | 6/2011 | Cohen et al. | |
| 2013/0089828 A1 * | 4/2013 | Borovinskih | A61C 7/08 433/6 |
| 2013/0095446 A1 * | 4/2013 | Andreiko | A61C 7/08 433/6 |
| 2013/0115567 A1 | 5/2013 | Jasper | |
| 2013/0122448 A1 * | 5/2013 | Kitching | A61C 7/002 433/24 |
| 2013/0157213 A1 * | 6/2013 | Arruda | A61C 7/08 433/6 |
| 2013/0230819 A1 * | 9/2013 | Arruda | A61C 7/22 433/6 |
| 2014/0178829 A1 * | 6/2014 | Kim | A61C 7/36 433/3 |
| 2015/0079531 A1 * | 3/2015 | Heine | A61C 7/36 433/19 |
| 2015/0238284 A1 * | 8/2015 | Wu | A61C 7/002 433/19 |

* cited by examiner

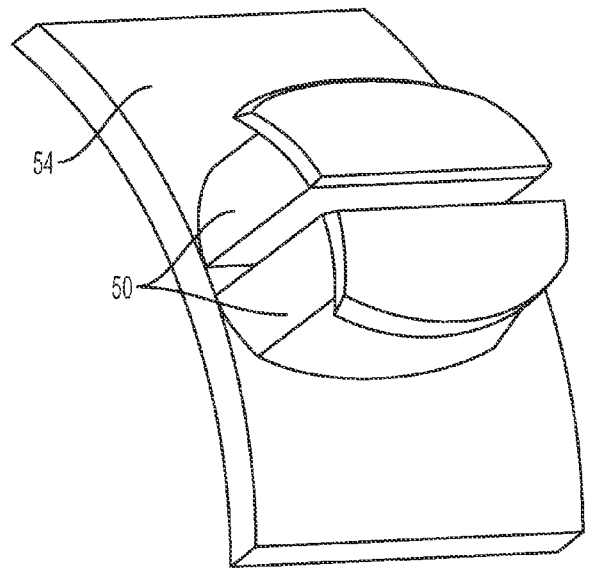 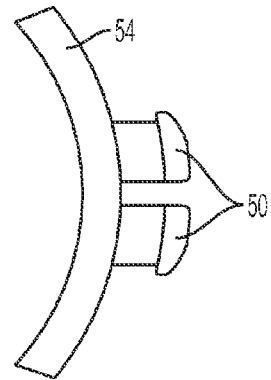
FIG. 6A  FIG. 6B
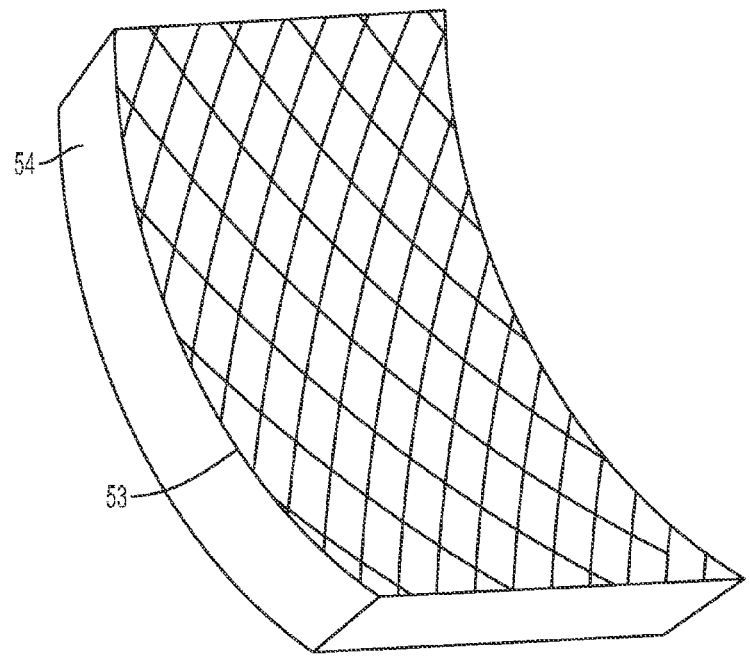
FIG. 6C

CLASS II MALOCCLUSION CORRECTION APPLIANCE FOR REMOVABLE ALIGNERS

CROSS REFERENCE TO RELATED APPLICATIONS

The present application claims priority to U.S. Provisional Patent Application No. 62/047,386, filed Sep. 8, 2014, entitled "Class II Malocclusion Correction Appliance for Removable Aligners," the entire disclosure of which is hereby incorporated by reference in its entirety.

TECHNICAL FIELD

This disclosure relates to orthodontic appliances and, more particularly, to Class II malocclusion correction appliances.

BACKGROUND

The incorrect positioning of teeth or the misalignment of teeth between the upper dental arch and lower dental arch are known as malocclusions. Dental health professionals generally categorize malocclusions into three classifications designated as Class I, Class II, and Class III. Class I malocclusions are those in which the individual teeth are not aligning well with each other and/or corresponding teeth in the opposite jaw, for example due to spacing or crowding problems. Class II malocclusions relate to those cases in which the upper jaw is not properly positioned relative to the lower jaw, resulting in the upper teeth projecting in front of the lower teeth. The excess horizontal overlap of upper teeth to the lower teeth in this type of malocclusion is typically referred to as excess overjet. Class III malocclusions occur when the lower jaw is positioned too far forward with respect to the upper jaw. This type of malocclusion is typically referred to as an underbite.

The most frequently treated type of malocclusion is the Class I malocclusion. Historically, practitioners treated Class I malocclusions by applying braces to a patient's teeth. This involves placing brackets on individual teeth and connecting the brackets with an archwire to guide movement of the teeth into desired alignment. More recently, removable alignment devices have entered the marketplace as a substitute for the traditional fixed-style braces. These removable alignment devices are designed to be placed over a patient's teeth and have teeth-receiving cavities shaped to receive and apply a resilient positioning force to the patient's teeth. Over a course of treatment, a series of preformed aligners are provided that gradually move the location of the teeth-receiving cavities and, correspondingly, the patient's teeth until the teeth are in a desired alignment. One of the most commercially successful versions of this removable alignment type device is sold under the tradename Invisalign®.

While both fixed braces and removable aligners are suitable for correcting Class I malocclusions, the devices cannot be used alone to correct Class II and Class III malocclusions. Rather, additional orthodontic appliances must be used to force the jaw into its proper bite position by forcing the jawbones and muscles to physically adjust to the proper bite position. For patients wearing fixed braces, the brace hardware can provide an architectural platform for attaching springs, rubber bands, or other appliances that apply a force to move the upper jaw and lower jaw into proper relative alignment. This architectural platform is not present on patients undergoing treatment with a removable aligner system. Moreover, because the aligners for these patients are designed to be removable, any supplemental correction forces applied to the aligners such as traditional orthodontic elastics can have a tendency to pull the aligners away from a patient's teeth, limiting the effectiveness of the treatment.

SUMMARY

In general, this disclosure is directed to malocclusion correction appliances for use with removable aligners. In some examples, a malocclusion correction appliance has an adjustable length body that is connectable at one end to a patient's upper removable aligner and at an opposite end to the patient's lower removable aligner. For example, the malocclusion correction appliance may have connectors on its ends that engage with corresponding connectors on the patient's upper and lower removable aligners to connect the appliance to the aligners. The malocclusion correction appliance may also have a biasing member that functions to push opposite ends of the appliance away from each other. For example, the malocclusion correction appliance may have two segments that translate relative to each other between a retracted position in which the overall length of the correction appliance is comparatively short and an extended position in which the overall length is comparatively long. The biasing member in such a configuration can attach to the two segments so as to push the ends of the two segments away from each other. During use, the biasing force applied to the two segments of the corrector can translate through the patient's upper and lower removable aligners via the connected ends of the corrector. In turn, this can push the patient's lower set of teeth and lower jaw forward relative to the patient's upper set of teeth and upper jaw, treating a Class II malocclusion.

By configuring the correction appliance to push on the patient's upper and lower removable aligners rather than pull on the aligners, the correction appliance has a tendency to further push the aligners onto the patient's teeth rather than pull the aligners away from the teeth. This can keep the aligners properly seated to perform their intended tooth alignment function while also providing Class II malocclusion correction. In typical configurations, the patient may remove and reinsert the hardware from their mouth by themselves, including the malocclusion correction appliance and the upper and lower removable aligners. This can allow the patient to remove the hardware when desired and reinsert the hardware at a later time.

Depending on a desired course of treatment, a dental health professional may use a system with multiple malocclusion correction appliances in accordance with the disclosure to treat a patient's Class II malocclusion. The system may include multiple pairs of malocclusion correction appliances, with one correction appliance in each pair being used for the right and left sides of a patient's mouth, respectively. Each pair of malocclusion correction appliances may have a different maximum length. A comparatively short pair of malocclusion correction appliances may be used at the beginning of treatment when the patient's top jaw is offset the most from the patient's bottom jaw. As the patient's top and bottom jaws are moved into closer alignment over the course of treatment, the dental health professional may use progressively longer pairs of malocclusion correction appliances. Depending on the application, a dental health professional may use multiple pairs of malocclusion correction appliances having different lengths with a single set of upper and lower removable aligners. For example, either the dental health professional or patient may detach one pair of correction appliances from the upper and lower removable aligners and attach another pair of correction appliances having a longer maximum length to the aligners. Alternatively, each pair of malocclusion correction appliances may be attached to a different set of upper and lower removable aligners, such as a different set of aligners within a progressive course of treatment using multiple sets of removable aligners.

In one example, an orthodontic appliance system is described that includes a first removable orthodontic aligner, a second removable orthodontic aligner, and an orthodontic appliance. The first removable orthodontic aligner is configured to be positioned over a patient's upper set of teeth. The second removable orthodontic aligner is configured to be positioned over the patient's lower set of teeth. The orthodontic appliance is connected at one end to the first removable orthodontic aligner and at an opposite end to the second removable orthodontic aligner. According to the example, the orthodontic appliance has an elongated body of adjustable length and a biasing member configured to push opposed ends of the elongated body away from each other, such that when the first removable orthodontic aligner is positioned over the patient's upper set of teeth and the second removable orthodontic aligner is positioned over the patient's lower set of teeth, the orthodontic appliance moves the patient's lower set of teeth forward relative to the patient's upper set of teeth to treat a Class II malocclusion.

In another example, a malocclusion correction system is described that includes at least one set of removable orthodontic aligners and a plurality of pairs of orthodontic appliances. The set of removable orthodontic aligners includes a first removable orthodontic aligner configured to be positioned over a patient's upper set of teeth and a second removable orthodontic aligner configured to be positioned over the patient's lower set of teeth. In addition, the first removable orthodontic aligner includes a right side connector and a left side connector and the second removable orthodontic aligner also includes a right side connector and a left side connector. According to the example, each of the plurality of pairs of orthodontic appliances have a different maximum length, and each orthodontic appliance within each pair of orthodontic appliances is configured to releasably connect to the right side connector of the first removable orthodontic aligner and the right side connector of the second removable orthodontic aligner or the left side connector of the first removable orthodontic aligner and the left side connector of the second removable orthodontic aligner. The example also specifies that each orthodontic appliance has an elongated body of adjustable length and a biasing member configured to push opposed ends of the elongated body away from each other, such that when the first removable orthodontic aligner is positioned over the patient's upper set of teeth and the second removable orthodontic aligner is positioned over the patient's lower set of teeth, the orthodontic appliance moves the patient's lower set of teeth move forward relative to the patient's upper set of teeth to treat a Class II malocclusion.

In another example, a method is described that includes selecting one pair of orthodontic appliances from a plurality of pairs of orthodontic appliances to provide a selected pair of orthodontic appliances, each of the plurality of pairs of orthodontic appliances having a different maximum length. The method also includes connecting one of the selected pair of orthodontic appliances to a right side connector of a first removable orthodontic aligner configured to be positioned over a patient's upper set of teeth and a right side connector of a second removable orthodontic aligner configured to be positioned over the patient's lower set of teeth. The method also includes connecting a remaining one of the selected pair of orthodontic appliances to a left side connector of the first removable orthodontic aligner and a left side connector of the second removable orthodontic aligner. According to the example, each orthodontic appliance in the plurality of pairs of orthodontic appliances has an elongated body of adjustable length and a biasing member configured to push opposed ends of the elongated body away from each other, such that when the first removable orthodontic aligner is positioned over the patient's upper set of teeth and the second removable orthodontic aligner is positioned over the patient's lower set of teeth, the orthodontic appliance moves the patient's lower set of teeth forward relative to the patient's upper set of teeth to treat a Class II malocclusion.

The details of one or more examples are set forth in the accompanying drawings and the description below. Other features, objects, and advantages will be apparent from the description and drawings, and from the claims.

BRIEF DESCRIPTION OF DRAWINGS

FIGS. 6A-C and 7 are illustrations of example configurations of corresponding connector features that can be used to connect an orthodontic appliance according to the disclosure to a removable orthodontic aligner.

DETAILED DESCRIPTION

In general, this disclosure relates to an orthodontic correction appliance for use with removable orthodontic aligners to treat Class II malocclusions. In some examples, the correction appliance has two elongated sections that are slidably connected to each other and allowed to move back and forth relative to each other. The ends of the two elongated sections can be attached to connectors extending from the removable aligners. In addition, the ends of the two elongated sections can move toward and away from each other to allow the orthodontic appliance to extend and contract in length during use. This can be useful to allow the patient to open and close their mouth when the removable aligners are installed over their teeth and the correction appliance(s) is attached to the aligners.

To provide a corrective force causing the lower jaw of the patient to move forward relative to the upper jaw to treat the Class II malocclusion, the corrective appliance may carry a biasing member that is connected to each of the two elongated sections of the appliance. The biasing member may bias the ends of the two elongated sections away from each other. For example, the biasing member may tend to push the ends of the two elongated sections away from each other to their maximum extent, forcing the patient to apply a counterforce against the biasing member to shorten the length of the corrective appliance in order to close their mouth.

By configuring the orthodontic correction appliance to connect directly to the removable orthodontic aligners, a dental practitioner can simultaneously treat a patient with Class I and Class II malocclusions while still providing the patient with the conveniences of removable aligners. The removable orthodontic aligners can realign the patient's individual teeth while the orthodontic correction appliance works to treat the patient's excess overjet by moving the upper jaw into proper alignment with the lower jaw.

Example orthodontic corrective appliance configurations will be described in greater detail with respect to FIGS. 2-4. However, an example removable orthodontic aligner that can be used in conjunction with an orthodontic corrective appliance will first be described with reference to FIG. 1.

Figure 1:
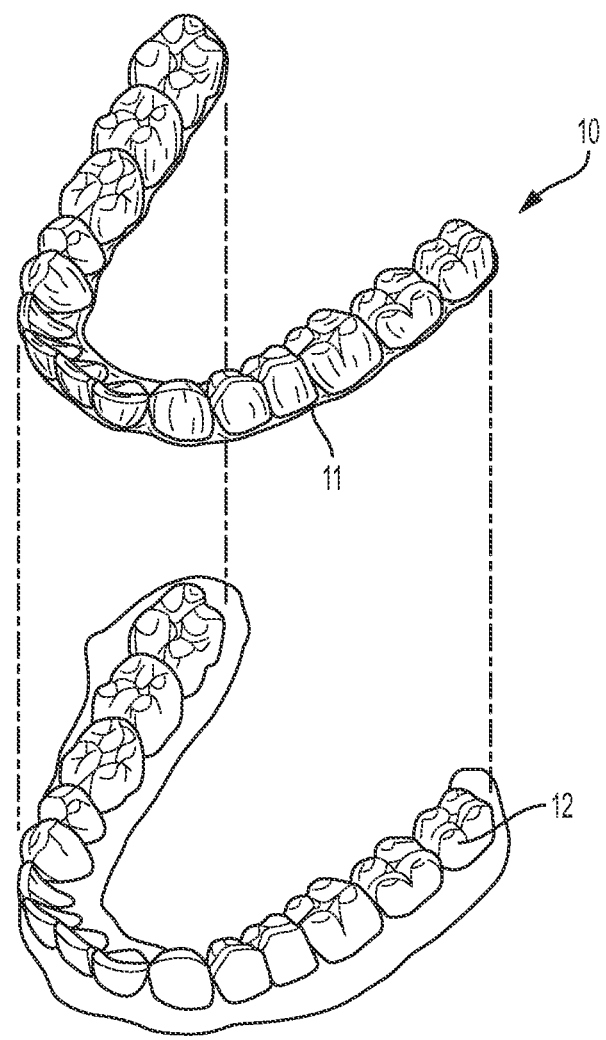
FIG. 1 is an illustration of an example removable orthodontic aligner that can be used in conjunction with an orthodontic corrective appliance according to the disclosure.

FIG. 1 is an illustration of an example removable orthodontic aligner 10 that can be connected to an orthodontic corrective appliance according to the disclosure. Removable orthodontic aligner 10 defines a concave trough 11 configured to conform to a patient's set of teeth 12. Removable orthodontic aligner 10 has a number of individual tooth-shaped segments corresponding to the patient's set of teeth 12. The individual tooth-shaped segments can be configured (e.g., sized and/or shaped) to move at least some of the teeth 12 from an initial tooth arrangement to a final tooth arrangement. Examples of commercially available aligners that can be used as removable orthodontic aligner 10 include those marked under the tradenames Invisalign® and ClearCorrect™, which provide a clear polymeric shell that is installed over a patient's teeth. Although FIG. 1 only illustrates a single removable aligner for a single set of teeth 12, in practice, a patient would typically be provided with one aligner for an upper set of teeth and one aligner for a lower set of teeth.

In use, removable orthodontic aligner 10 is positioned over the patient's set of teeth 12 and, in different examples, can be sized to enclose all of the patient's teeth within a set or a lesser number of teeth. Once positioned over the patient's set of teeth 12, removable orthodontic aligner 10 may be held in place by frictional engagement with the surfaces of the teeth and/or the surfaces of the patient's mouth, allowing the patient to manually remove the aligner by simply lifting the aligner back off the teeth. Removable orthodontic aligner 10 can be configured so that only certain teeth within an enclosed set are repositioned at any one time, while other teeth within a set provide a base or anchor region for holding a repositioning appliance in the aligner in place to apply a resilient repositioning force against the tooth or teeth to be repositioned. In complex cases, many or most of the teeth may be repositioned at some point during the treatment. In such cases, the teeth that are moved can subsequently serve as a base or anchor region for holding a repositioning appliance during later treatment sessions. Additionally or alternatively, the gums and/or the palette of the patient can serve as an anchor region, thus allowing all or nearly all of the teeth to be repositioned simultaneously.

To provide a course of treatment, progressive sets of aligners (e.g., where each set include an upper tooth set aligner and lower tooth set aligner) can be provided in which each set more aggressively biases a patient's teeth toward an ideal occlusion. Orthodontic patients undergoing such progressive treatment may wear, for example, from between 15 to 25 sets of progressive aligners. Over a period of time, sequential and progressively biased positioners can move teeth from their initial maloccluded positions to a near finished and corrected state.

In applications where Class II malocclusion correction treatment is desired in conjunction with using a set of removable orthodontic aligners 10, an orthodontic appliance can be connected to an outside surface of an upper removable aligner and a lower removable aligner. FIG. 2 is an illustration of an example orthodontic appliance 20 that can be used to provide Class II malocclusion correction treatment in conjunction with a set of removable orthodontic aligners, such as removable orthodontic aligners 10. FIG. 2 illustrates an example arrangement in which orthodontic appliance 20 is attached on the left side of a patient's mouth (i.e., from the patient's reference point). In practice, a dental health practitioner may attach an identical orthodontic aligner at corresponding attachment locations on the right side of the patient's mouth so the patient has aligners on both the left and right sides of their mouth. Alternatively, an orthodontic aligner may be placed only on the left or right side of the patient's mouth.

Figure 2:
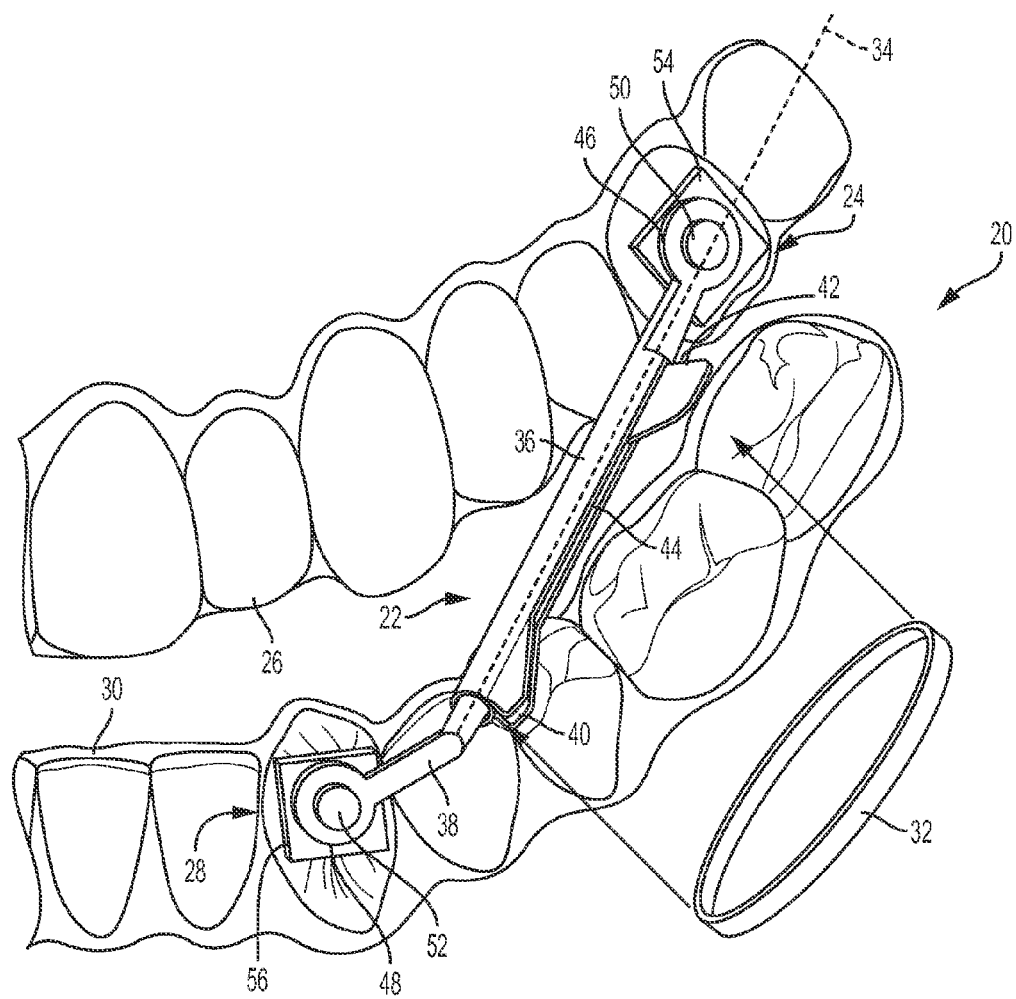
FIG. 2 is an illustration of an example orthodontic appliance that can be used to provide Class II malocclusion correction treatment in conjunction with a set of removable orthodontic aligners.
Figure 3:
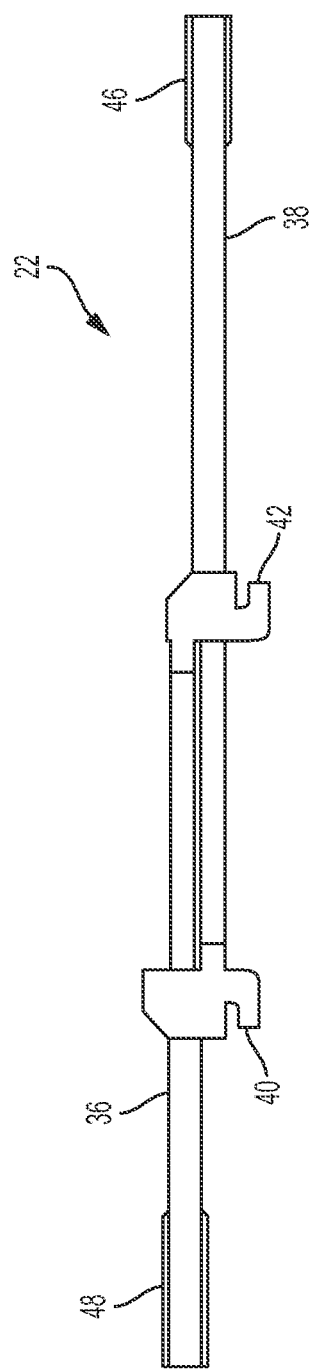
FIG. 3 is an illustration of another example configuration of an example orthodontic appliance that can be used to provide Class II malocclusion correction treatment in conjunction with a set of removable orthodontic aligners.

In the example of FIG. 2, orthodontic appliance 20 includes an elongated body 22 extending from a first connector 24 connected to first removable aligner 26 positioned over a patient's upper set of teeth to a second connector 28 connected to a second removable aligner 30 positioned over a patient's lower set of teeth. Orthodontic appliance 20 also includes a biasing member 32, which is illustrated as being separate from but attachable to elongated body 22. Elongated body 22 has an adjustable length along its major axis 34, allowing the elongated body to extend and contract in length relative to fixed connection points provided by first connector 24 and second connector 28.

In use, biasing member 32 is connected to elongated body 22 to cause opposed ends of the elongated body to bias away from each other. The biasing force can cause opposed ends of elongated body 22 to push away from each other, pushing one end of the elongated body in a generally upward and backward direction into first removable aligner 26 and the opposite end of the elongated body in a generally downward and forward direction into second removable aligner 30. Over time, the pushing force tends to move the patient's lower set of teeth and lower jaw forward relative to the patient's upper set of teeth and upper jaw, and push the patient's upper set of teeth and upper jaw backward relative to the patient's lower set of teeth and lower jaw, thus providing Class II malocclusion correction.

In the configuration of FIG. 2, elongated body 22 includes a first elongated section 36 terminating at first connector 24 and a second elongated section 38 terminating at second connector 28. First elongated section 36 and second elongated section 38 are slidably connected to each other and movable relative to each other between a retracted position in which elongated body 22 is comparatively short and an extended position in which elongated body is comparatively long. First elongated section 36 and second elongated section 38 can overlap with each other a varying amount to allow the overall length of elongated body 22 to extend and contract. For example, in FIG. 2, first elongated section 36 and second elongated section 38 are coaxially aligned. Further, first elongated section 36 and second elongated section 38 have complementary shapes but different sizes such that second elongated section 38 is insertable into and retractable from an interior of first elongated section 36. During use, second elongated section 38 can nest inside of first elongated section 36 (as illustrated in FIG. 2) when the patient closes their mouth, decreasing the distance separating first connector 24 from second connector 28 and thereby contracting the overall length of elongated body 22. By contrast, when the patient opens their mouth and increases the distance separating first connector 24 from second connector 28, second elongated section 38 can withdraw at least partially, and in some examples fully, from first elongated section 36 to extend the overall length of elongated body 22.

In different examples, first elongated section 36 may be insertable into and retractable from an interior of second elongated section 38 rather than the opposite arrangement illustrated on FIG. 2. As another example, first elongated section 36 and second elongated section 38 may be positioned side-by-side rather than having one section nested inside of another section. FIG. 3 is an illustration of an example configuration of orthodontic appliance 20 showing first elongated section 36 positioned side-by-side with second elongated section 38 rather than in a nested configuration.

With further reference to FIG. 2, biasing member 32 is configured to be connected to first elongated section 36 and second elongated section 38 to provide a force that biases opposed ends of elongated body 22 away from each other. Biasing member 32 may provide a force that translates through first removable aligner 26 and second removable aligner 30 via first connector 24 and second connector 28 and acts on the patient's upper jaw and lower jaw. For example, when the patient's mouth is closed, biasing member 32 may provide a substantially constant force acting on the patient's upper set of teeth and corresponding upper jaw and lower set of teeth and corresponding lower jaw, pushing the patient's lower set of teeth forward relative to the patient's upper set of teeth to treat excess overjet. The magnitude of the force acting on the patient's upper jaw and the lower jaw may increase when the patient opens their mouth and biasing member 32 is extended, for example, elastically.

In different examples, biasing member 32 may be implemented using a rubber band, a spring, or any other suitable biasing member. While biasing member is shown in FIG. 2 as an element applied to or coupled to the exterior of an orthodontic appliance, an internal mechanism may be used, such as a spring, to push the opposing elements of the orthodontic appliance away from each other.

In the example of FIG. 2, biasing member 32 is illustrated as being a rubber band. First elongated section 36 and second elongated section 38 can each have an attachment portion or attachment feature to attach ends of biasing member 32 to the elongated sections. In the configuration of FIG. 2, first elongated section 36 carries a first hook 40 and second elongated section 38 carries a second hook 42. First hook 40 is positioned adjacent to a distal end of first elongated section 36 opposite first connector 24. Second hook 42 is positioned adjacent a distal end of second elongated section 38 opposite second connector 28. First hook 40 and second hook 42 may each be a curved or angled portion of the respective elongated sections about which a rubber band biasing member can be positioned.

In use, biasing member 32 may be stretched from an equilibrium length to an elastically deformed length and positioned around first hook 40 and second hook 42. The distance separating first hook 40 from second hook 42 may be greater than the equilibrium length of biasing member 32 such that the biasing member provides a force pulling first hook 40 toward second hook 42. As first hook 40 and second hook 42 are pulled toward each other, the opposite ends of first elongated section 36 and second elongated section 38 are pushed away from each other. This pushing force can have a tendency to further push first removable aligner 26 and second removable aligner 30 onto the patient's teeth rather than pull the aligners away from the teeth. Further, this push force can push the patient's lower set of teeth and lower jaw forward relative to the patient's upper set of teeth and upper jaw, treating the patient's excess overjet.

When first elongated section 36 and second elongated section 38 include first hook 40 and second hook 42, respectively, the hooks may be arranged on the elongated bodies in such a way that the hooks can move relative to each other when the patient opens and closes their mouth. For example, when elongated body 22 is configured so one elongated section is insertable into and retractable from an interior of the other elongated section, the exterior member may include a slot extending along at least a portion of its longitudinal length. The hook of the interior elongated section can project through the slot and travel along the slot as the overall length of elongated body 22 is adjusted, e.g., when a patient opens and closes their mouth.

In the configuration of FIG. 2, first elongated section 36 includes a slot 44 extending along its longitudinal length between first connector 24 and first hook 40. Second hook 42 of second elongated section 38 extends through slot 44. When a patient opens and closes their mouth, second hook 42 can travel back and forth in slot 44 to adjust the overall length of elongated body 22. In some examples, first elongated section 36 and/or second elongated section 38 includes a detent, mechanical stop, or other limiting feature that prevents first elongated section 36 and second elongated section 38 from translating past the terminal ends of each other, which may otherwise cause separation of elongated body 22 into two or more physically separate components.

To facilitate connection between orthodontic appliance 20 and first and second removable aligners 26 and 30, the orthodontic appliance and removable aligners can have corresponding connection features. The connection features can enable elongated body 22 to be attached at one end to first removable aligner 26 and at the opposite end to second removable aligner 30. The connection features may be configured so that orthodontic appliance 20 can rotate relative to first and second removable aligners 26 and 30, e.g., when the patient open and closes their mouth. The connection features can provide points through which forces generated by biasing member 32 translate to the patient's upper set of teeth and lower set of teeth. Depending on the design, the connections between orthodontic appliance 20 and first and second removable aligners 26 and 30 can be permanent, for example, such that orthodontic appliance 20 cannot be removed from the aligners without damaging the material structure of one or more of the components. Alternatively, the connections between orthodontic appliance 20 and first and second removable aligners 26 and 30 can be releasable. In such an application, orthodontic appliance 20 may be repeatedly attached to and detached from first and second removable aligners 26 and 30. Configuring orthodontic appliance 20 to be releasable from first and second removable aligners 26 and 30 may be useful to enable a user to separately remove the orthodontic appliance and removable aligners from their mouth rather than having to remove the entire assembly at once. Configuring orthodontic appliance 20 to be releasable from first and second removable aligners 26 and 30 may also be useful to facilitate attachment and detachment of different orthodontic appliances (e.g., different sized orthodontic appliances) to a set of removable aligners and/or different sets of removable aligners to a specific orthodontic appliance during a course of treatment.

Any suitable mechanical fixation elements can be used to connect orthodontic appliance 20 to first and second removable aligners 26 and 30. In the example of FIG. 2, orthodontic appliance 20 includes a connective aperture 46 positioned on a terminal end of first elongated section 36 and another connective aperture 48 positioned on a terminal end of second elongated section 38. In addition, first removable aligner 26 includes a pin 50 extending outwardly away from an external surface of the aligner that is configured to be received by connective aperture 46. Second removable aligner 30 also includes a pin 52 extending outwardly away from an external surface of the aligner that is configured to be received by connective aperture 48. Pins 50 and 52 are connected to bases 54 and 56, respectively, which may be adhered to the external surfaces of the aligners. To establish first connector 24 and second connection 28, a user can push connective aperture 46 over the distal end of pin 50 and similarly push connective aperture 48 over the distal end of pin 52. In some examples, pins 50 and 52 can have a distal head of larger cross-sectional area than the remainder of the pins. The enlarged distal heads may prevent connective apertures 46 and 48 from unintentionally detaching from pins 50 and 52 during subsequent use. Alternatively, a locking clip, locking nut, or other locking feature may be used to prevent the connective apertures from unintentionally detaching from the pins. In still other examples, first elongated section 36 and second elongated section 38 may not have connective apertures but may instead carry connective pins configured to be inserted into corresponding apertures on first removable aligner 26 and second removable aligner 30.

Figure 4:
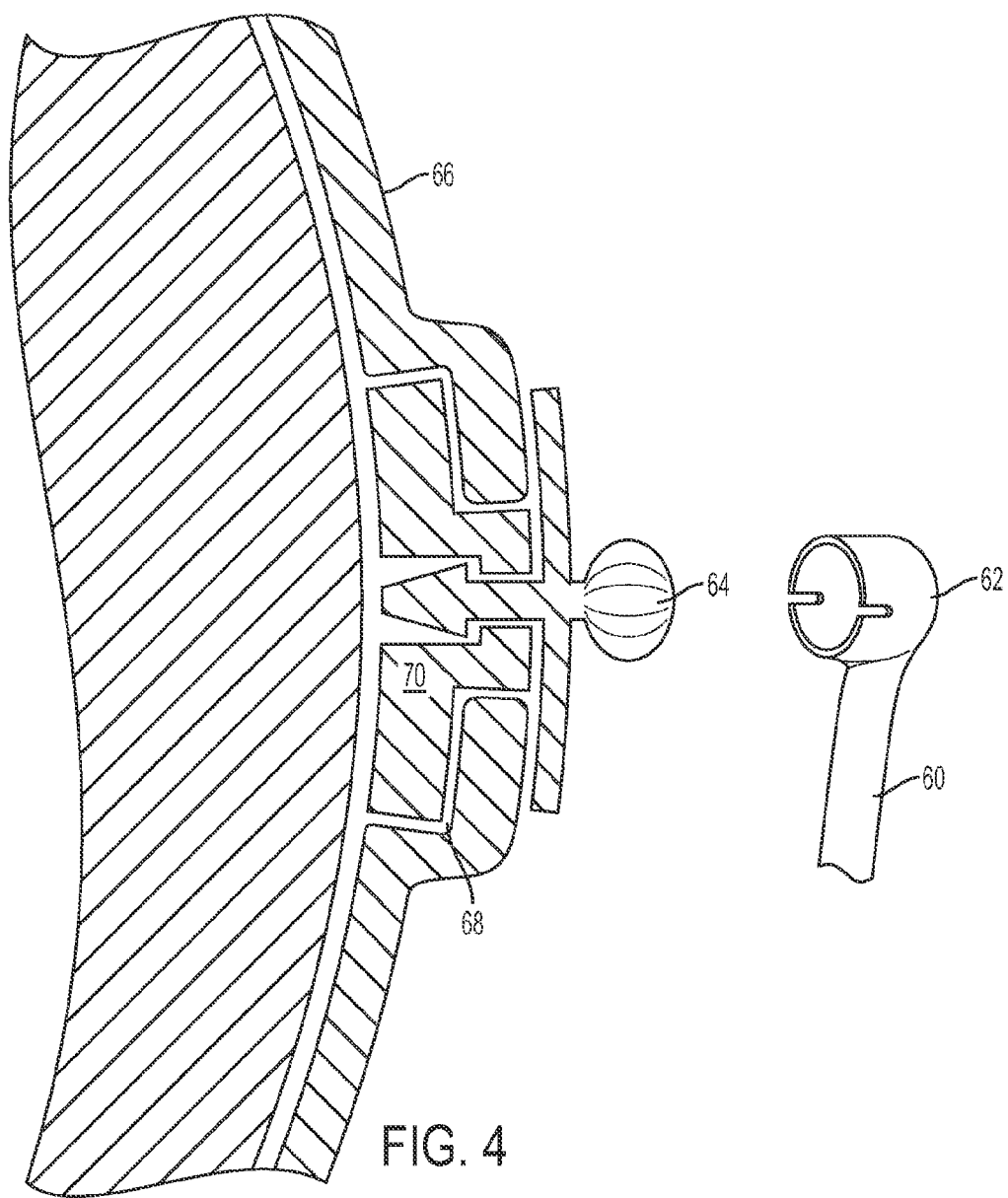
FIG. 4 is an illustration of an example configuration of corresponding connector features that can be used to connect an orthodontic appliance according to the disclosure to a removable orthodontic aligner.

FIG. 4 is an illustration of an example configuration of corresponding connector features that can be used to connect orthodontic appliance 20 to first removable aligner 26 and second removable aligner 30. In this example, an elongated member 60 is illustrated as having a terminal end 62 configured to connect to a pin 64 extending outwardly away from a removable aligner 66. Terminal end 62 defines a receiving cavity configured (e.g., sized and/or shaped) to receive pin 64. Terminal end 62 can be pushed onto pin 64 and frictional engagement can secure and releasably hold the terminal end on the pin.

Pin 64 can be secured to removable aligner 66 using any suitable techniques that prevent the pin from moving or breaking during use of the orthodontic appliance. In some examples, pin 64 is integrally and permanently formed with removable aligner 66, e.g., by casting or molding the pin simultaneously with casting or molding the removable aligner. In other examples, pin 64 is attached to removable aligner 66 after casing or molding the aligner. In the example of FIG. 4, removable aligner 66 includes a connector retaining pocket 68 extending outwardly from a remainder of the aligner that contains a connector retainer 70. Pin 64 is insertable through an aperture extending through a side wall of connector retaining pocket 68 of removable aligner 66. A proximal end of pin 64 engages with connector retainer 70 within connector retaining pocket 68 to secure the pin to the removable aligner.

To form a removable aligner having a retaining pocket and a connector retainer, an impression can be taken of a patient's teeth or the teeth can be digitally scanned. Prior to forming the impression or digitally scanning the teeth, a template pad can be temporarily bonded to the tooth of the patient in the region where pin 64 is desired to be positioned. Upon subsequently forming a removable aligner using an impression or digital scan generated while the patient was wearing the template pad, the removable aligner will include a retaining pocket corresponding to the location where the patient was wearing the template pad. An aperture can be bored through the retaining pocket and a connector retainer positioned in the pocket to connect to a pin. Of course, instead of physically attaching a template pad to generate a retaining pocket, the retaining pocket can instead by generated digitally using a computer when preparing a patient's removable aligners.

With further reference to FIG. 2, orthodontic appliance 20 can be connected at a variety of different locations on first removable aligner 26 and second removable aligner 30 relative to the patient's anatomy. The specific location where orthodontic appliance 20 mates with the removable aligners can be varied by changing the location of the connection features carried by first removable aligner 26 and second removable aligner 30. In general, to treat a Class II malocclusion using orthodontic appliance 20, the appliance is attached such that the end of elongated body 22 attached to the patient's upper removable liner is positioned behind (e.g., toward the back of the mouth) the end of the elongated body attached to the patient's lower removable aligner. This positioning tends to push the patient's lower set of teeth and jaw forward while pushing the patient's upper set of teeth and jaw backward, treating the patient's excess overjet.

In one example, orthodontic appliance 20 is configured to connect to first removable aligner 26 at a position corresponding to the patient's first molar and also connect to second removable aligner 30 at a position corresponding to the patient's second bicuspid. Other connection locations are possible in accordance with the disclosure, and it should be appreciated that the disclosure is not limited in this respect.

Pairs of orthodontic appliances in accordance with the disclosure may be used to provide simultaneous pushing forces to both the right and left sides of the patient's mouth during treatment. Depending on a desired course of treatment, a dental health professional may use multiple different pairs of orthodontic appliances to treat a patient's malocclusion. A comparatively long pair of malocclusion correction appliances may be used at the beginning of treatment when the patient's top jaw is offset the most from the patient's bottom jaw. As the patient's top and bottom jaws are moved into closer alignment over the course of treatment, the dental health professional may use progressively longer pairs of malocclusion correction appliances. For example, a difference in maximum length between a shortest one of the pairs of orthodontic appliances used during treatment and a longest one of the pairs of orthodontic appliances may range from approximately 8 millimeters to approximately 40 millimeters for a typical patient, such as from 10 millimeters to 30 millimeters.

During treatment, a patient's orthodontic appliances in accordance with the disclosure and removable aligners can be replaced with any suitable frequency. In some examples, a patient may use multiple pairs of malocclusion correction appliances having different lengths with a single set of upper and lower removable aligners. For example, either the dental health professional or patient may detach one pair of correction appliances from the upper and lower removable aligners and attach another pair of correction appliances having a longer maximum length to the aligners. In other examples, each pair of malocclusion correction appliances may be attached to a different set of upper and lower removable aligners, such as a different set of aligners within a progressive course of treatment using multiple sets of removable aligners.

Figure 5:
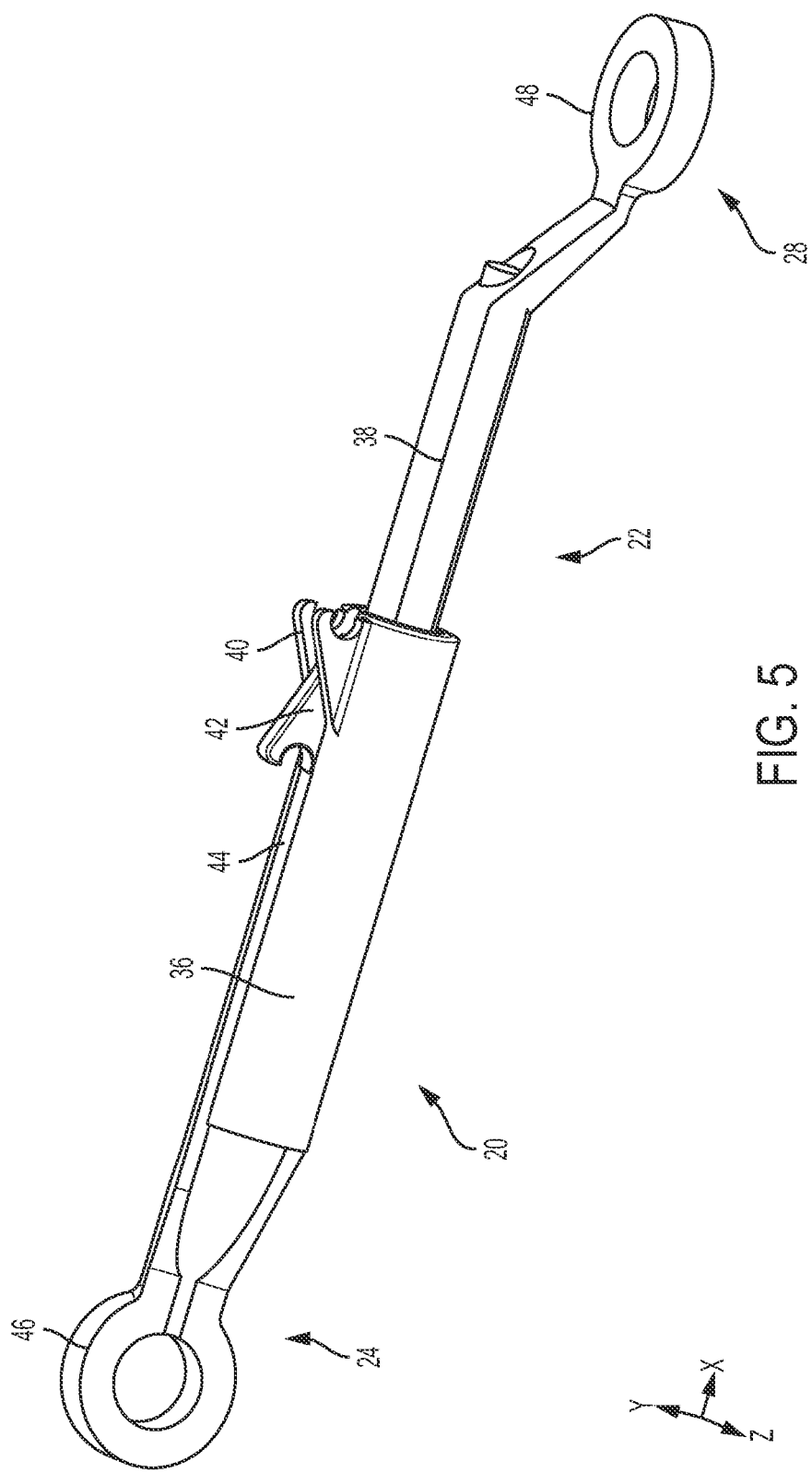
FIG. 5 is an illustration of another example configuration of an example orthodontic appliance that can be used to provide Class II malocclusion correction treatment in conjunction with a set of removable orthodontic aligners.

FIG. 5 is an illustration of another example configuration of an example orthodontic appliance 20 that can be used to provide Class II malocclusion correction treatment in conjunction with a set of removable orthodontic aligners, such as removable orthodontic aligners 10. Orthodontic appliance 20 includes an elongated body 22 extending from a first connector 24 connected to first removable aligner positioned over a patient's upper set of teeth to a second connector 28 connected to a second removable aligner positioned over a patient's lower set of teeth. Elongated body 22 has an adjustable length along its major axis (longitudinal axis) allowing the elongated body to extend and contract in length relative to fixed connection points provided by first connector 24 and second connector 28.

In use, a biasing member may be connected to elongated body 22 to cause opposed ends of the elongated body to bias away from each other. The biasing force can cause opposed ends of elongated body 22 to push away from each other, pushing one end of the elongated body in a generally upward and backward direction into a first removable aligner and the opposite end of the elongated body in a generally downward and forward direction into a second removable aligner. Over time, the pushing force tends to move the patient's lower set of teeth and lower jaw forward relative to the patient's upper set of teeth and upper jaw, and push the patient's upper set of teeth and upper jaw backward relative to the patient's lower set of teeth and lower jaw, thus providing Class II malocclusion correction.

In the configuration of FIG. 5, elongated body 22 includes a first elongated section 36 terminating at first connector 24 and a second elongated section 38 terminating at second connector 28. First elongated section 36 and second elongated section 38 are slidably connected to each other and movable relative to each other between a retracted position in which elongated body 22 is comparatively short and an extended position in which elongated body is comparatively long. First elongated section 36 and second elongated section 38 can overlap with each other a varying amount to allow the overall length of elongated body 22 to extend and contract. For example, in FIG. 5, first elongated section 36 and second elongated section 38 are coaxially aligned. Further, first elongated section 36 and second elongated section 38 have complementary shapes but different sizes such that second elongated section 38 is insertable into and retractable from an interior of first elongated section 36. As configured in FIG. 5, first elongated section 36 and second elongated section 38 cannot rotate with respect to each other. Further, first connector 24 and second connector 28 are configured substantially at right angles with respect to each other to align with a particular anatomy of a user's teeth.

During use, second elongated section 38 can nest inside of first elongated section 36 when the patient closes their mouth, decreasing the distance separating first connector 24 from second connector 28 and thereby contracting the overall length of elongated body 22. By contrast, when the patient opens their mouth and increases the distance separating first connector 24 from second connector 28, second elongated section 38 can withdraw at least partially, and in some examples fully, from first elongated section 36 to extend the overall length of elongated body 22.

In different examples, first elongated section 36 may be insertable into and retractable from an interior of second elongated section 38 rather than the opposite arrangement illustrated on FIG. 5.

In the configuration of FIG. 5, first elongated section 36 carries a first hook 40 and second elongated section 38 carries a second hook 42. First hook 40 is positioned adjacent to a distal end of first elongated section 36 opposite first connector 24. Second hook 42 is positioned adjacent a distal end of second elongated section 38 opposite second connector 28. First hook 40 and second hook 42 may each be a curved or angled portion of the respective elongated sections about which a biasing member, such as a rubber band, can be positioned.

Hooks 40, 42 are arranged on the elongated bodies in such a way that the hooks can move relative to each other when the patient opens and closes their mouth. For example, when elongated body 22 is configured so one elongated section is insertable into and retractable from an interior of the other elongated section, the exterior member may include a slot 44 extending along at least a portion of its longitudinal length. Hook 42 can project through slot 44 and travel along slot 44 as the overall length of elongated body 22 is adjusted, e.g., when a patient opens and closes their mouth.

FIGS. 6A-C and 7 are illustrations of example configurations of corresponding connector features that can be used to connect an orthodontic appliance according to the disclosure to a removable orthodontic aligner.

FIGS. 6A and 6B show a base 54 with a pin 50 configured to couple at one side (the curved/concave side) with a removable aligner and at pin 50 with a connector of an orthodontic appliance. Pin 50 extends outwardly away from the base 54 and thus outwardly away from an external surface of the aligner and is configured to be received by a connective aperture, such as aperture 46 shown in FIG. 2. Pin 50 is configured with two opposing portions of a pin with enlarged heads (overhanging portions) to secure the connector in place when in use. The opposing portions of the pin have a space there between permitting relative movement of the portions toward each other to enable placement of the connector over the pin 50. To establish a connection, a user can push a connector over the distal end of pin 50. As shown, pin 50 has a head with a larger cross-sectional area than the body of pin 50. The enlarged head may prevent the connector from unintentionally detaching from pin 50 during subsequent use.

FIG. 6C shows a surface 53 for bonding base 54 to an aligner. Surface 53 may be smooth, or may be roughened to enable better adherence to an aligner using an adhesive. In an embodiment, there may be a mesh or other material applied to surface 53 to improve adherence. Alternatively, an aligner bonding system such as Bond Aligner (from Reliance Orthodontic Products Inc.) may be used.

Figure 7:
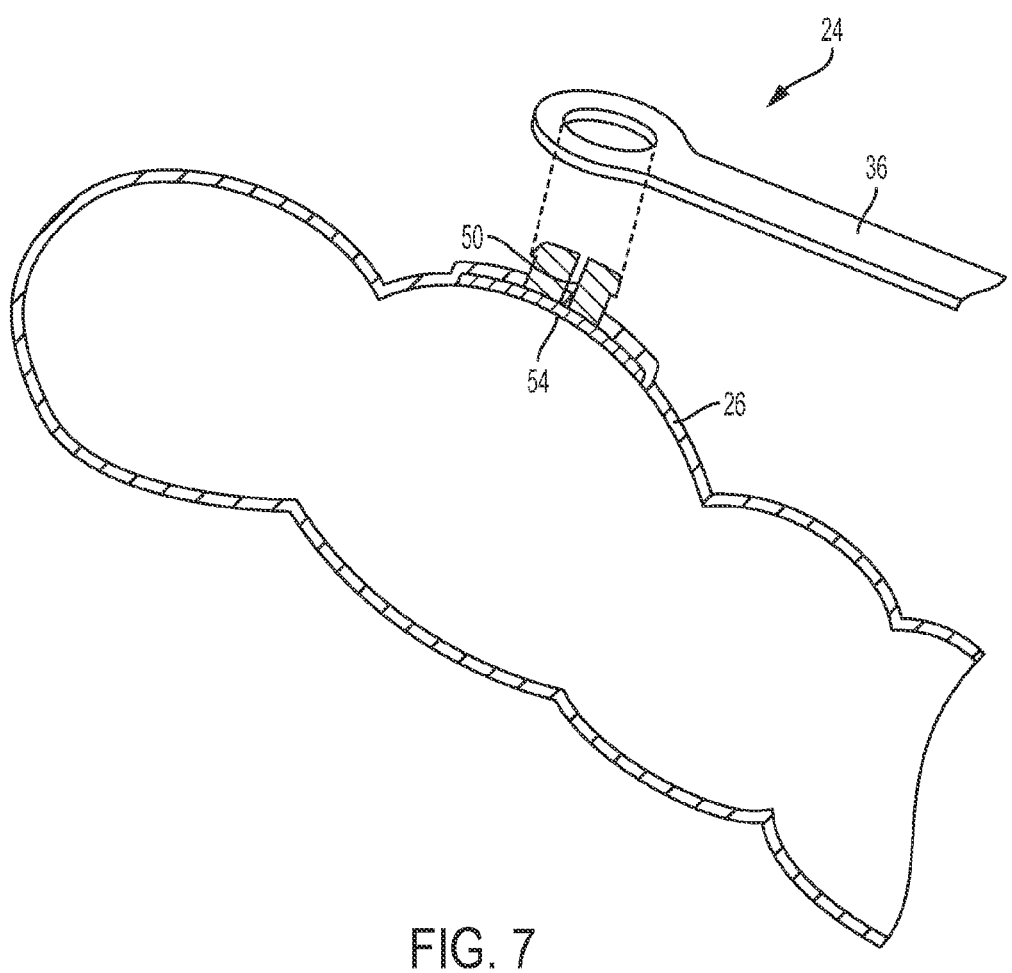

FIG. 7 illustrates an alternative attachment mechanism in which base 54 is applied internal to aligner 26 with pin 50 projecting through aligner 26. Pin 50 is then in a position to receive connector 24 of elongated section 36 (of an orthodontic appliance). Aligner 26 may have an interval reservoir that is shaped in a rectangular or other complementary dimension to fit the base 54. Pin 50 can be sized as appropriate to extend through aligner 26 and couple with connector 24.

Orthodontic appliances in accordance with embodiments herein may be constructed from a variety of materials, such as polymers. In embodiments, the material, or a component of a composition, may be selected to impart a desired color to the appliance, such as the same or similar color to teeth. Alternatively, an appliance may be made clear, such as provided for various removable aligners.

The orthodontic appliances may be constructed using any suitable manufacturing method such as molding or forming. In an embodiment, an appliance may be constructed using 3D printing to form one or more of the components.

Various examples have been described. These and other examples are within the scope of the following claims.

The invention claimed is:

1. An orthodontic appliance comprising:
   an elongated body of adjustable length comprising a first end and a second end, the elongated body comprising a first elongated section connected at the first end to a first removable orthodontic aligner and a second elongated section connected at the second end to a second removable orthodontic aligner, the first elongated section and the second elongated section being connected to and movable relative to each other between a retracted position and an extended position; and
   a biasing member configured to push the first and second ends of the elongated body away from each other, wherein the first elongated section comprises a first hook and the second elongated section comprises a second hook, and wherein the biasing member is configured to be coupled to the first hook and the second hook.

2. The orthodontic appliance of claim 1, wherein the first elongated section overlaps the second elongated section a varying amount such that a length of the elongated body is adjustable.

3. The orthodontic appliance of claim 1, wherein the first elongated section and the second elongated section are coaxially aligned.

4. The orthodontic appliance of claim 1, wherein the biasing member comprises a rubber band configured to be positioned around the first hook and the second hook.

5. The orthodontic appliance of claim 1, wherein one of the first elongated section and the second elongated section comprises a slot extending along at least a portion of its longitudinal length and a hook of the other of the first elongated section and the second elongated section extends through the slot and is configured to travel along the slot to adjust a length of the elongated body.

6. The orthodontic appliance of claim 1, wherein the orthodontic appliance is configured to be connected to the first removable orthodontic aligner at a position corresponding to a first molar and the orthodontic appliance is configured to be connected to the second removable orthodontic aligner at a position corresponding to a second bicuspid.

7. The orthodontic appliance of claim 1, wherein the orthodontic appliance is configured to be releasably connected to the first removable orthodontic aligner and the second removable orthodontic aligner such that the orthodontic appliance is configured to be disconnected from the first removable orthodontic aligner and the second removable orthodontic aligner and replaced with a different sized orthodontic appliance.

8. The orthodontic appliance of claim 1, wherein the first and second ends of the orthodontic appliance each comprise an aperture configured to be inserted onto a corresponding pin on each removable orthodontic aligner to secure the orthodontic appliance to the first removable orthodontic aligner and second removable orthodontic aligner.

9. The orthodontic appliance of claim 1, wherein the orthodontic appliance is configured to be rotatably connected to the first removable orthodontic aligner and second removable orthodontic aligner such that the orthodontic appliance is configured to rotate relative to the first removable orthodontic aligner and second removable orthodontic aligner.

10. The orthodontic appliance of claim 1, wherein the orthodontic appliance comprises a first orthodontic appliance configured to be connected on one side of the first removable orthodontic aligner and the second removable orthodontic aligner, and a second orthodontic appliance configured to be connected on an opposite side of the first removable orthodontic aligner and the second removable orthodontic aligner.

11. A malocclusion correction system comprising:
    at least one set of removable orthodontic aligners, the at least one set of removable orthodontic aligners including a first removable orthodontic aligner configured to be positioned over a patient's upper set of teeth and a second removable orthodontic aligner configured to be positioned over the patient's lower set of teeth, the first and second removable orthodontic aligners each comprising a right side connector and a left side connector;
    a plurality of pairs of orthodontic appliances, each of the plurality of pairs of orthodontic appliances having a different maximum length, and each orthodontic appliance having an elongated body of adjustable length and a biasing member configured to push opposed ends of the elongated body away from each other;
    wherein each elongated body comprises a first elongated section configured to releasably connect to at least one of the right side connector and the left side connector of the first removable orthodontic aligner and a second elongated section configured to releasably connect to at least one of the right side connector and the left side connector of the second removable orthodontic aligner, the first elongated section and the second elongated section being connected to and movable relative to each other;
    wherein each first elongated section comprises a first hook, each second elongated section comprises a second hook, and wherein the biasing member is configured to couple to the first hook and the second hook,
    wherein when the first removable orthodontic aligner is positioned over the patient's upper set of teeth and the second removable orthodontic aligner is positioned over the patient's lower set of teeth, the orthodontic appliance is configured move the patient's lower set of teeth forward relative to the patient's upper set of teeth so as to treat a Class II malocclusion.

12. The system of claim 11, wherein the at least one set of removable orthodontic aligners comprises a plurality of sets of removable orthodontic aligners, each of the plurality of sets of removable orthodontic aligners being configured for use with a different one of the plurality of pairs of orthodontic appliances.

13. The system of claim 11, wherein a difference in maximum length between a shortest one of the plurality of pairs of orthodontic appliances and a longest one of the plurality of pairs of orthodontic appliances ranges from approximately 8 millimeters to approximately 40 millimeters.

14. The system of claim 11, wherein the first elongated section overlaps the second elongated section a varying amount such that a length of the elongated body is adjustable.

15. The system of claim 11, wherein the first elongated section and the second elongated section are coaxially aligned.

16. The system of claim 11, wherein the biasing member comprises a rubber band configured to be positioned around the first hook and the second hook.

17. The system of claim 11, wherein one of the first elongated section and the second elongated section comprises a slot extending along at least a portion of its longitudinal length and a hook of the other of the first elongated section and the second elongated section extends through the slot and is configured to travel along the slot to adjust a length of the elongated body.

18. The system of claim 11, wherein the right side connector and left side connector of the first removable orthodontic aligner are located at a position corresponding to a first molar of the patient and the right side connector and left side connector of the second removable orthodontic aligner are located at a position corresponding to a second bicuspid of the patient.

19. The system of claim 11, wherein the right side connector and left side connector of the first removable orthodontic aligner and the right side connector and left side connector of the second removable orthodontic aligner each comprise a pin and opposed ends of each orthodontic appliance each comprise an aperture configured to be inserted onto the pin so as to secure the orthodontic appliance to the first removable orthodontic aligner and second removable orthodontic aligner.

20. The system of claim 11, wherein each pair of orthodontic appliances is configured to be releasably and rotatably connected to the right side connector of the first removable orthodontic aligner and the right side connector of the second removable orthodontic aligner or the left side connector of the first removable orthodontic aligner and the left side connector of the second removable orthodontic aligner, such that when connected, the orthodontic appliance is configured to rotate relative to the first removable orthodontic aligner and second removable orthodontic aligner when the patient opens and closes their mouth.

21. A method comprising:
selecting one pair of orthodontic appliances from a plurality of pairs of orthodontic appliances to provide a selected pair of orthodontic appliances, each of the plurality of pairs of orthodontic appliances have a different maximum length;
connecting one of the selected pair of orthodontic appliances to a right side connector of a first removable orthodontic aligner configured to be positioned over a patient's upper set of teeth and a right side connector of a second removable orthodontic aligner configured to be positioned over the patient's lower set of teeth; and
connecting a remaining one of the selected pair of orthodontic appliances to a left side connector of the first removable orthodontic aligner and a left side connector of the second removable orthodontic aligner,
wherein each orthodontic appliance in the plurality of pairs of orthodontic appliances has an elongated body of adjustable length and a biasing member configured to push opposed ends of the elongated body away from each other;
wherein each elongated body comprises a first elongated section and a second elongated section that are connected to and movable relative to each other, and wherein the first elongated section comprises a first hook, the second elongated section comprises a second hook, and the biasing member is configured to couple to the first hook and the second hook; and
wherein when the first removable orthodontic aligner is positioned over the patient's upper set of teeth and the second removable orthodontic aligner is positioned over the patient's lower set of teeth, the orthodontic appliance is configured to move the patient's lower set of teeth forward relative to the patient's upper set of teeth so as to treat a Class II malocclusion.

22. The method of claim 21, wherein a difference in maximum length between a shortest one of the plurality of pairs of orthodontic appliances and a longest one of the plurality of pairs of orthodontic appliances ranges from 10 millimeters to 30 millimeters.

23. The method of claim 21, wherein the first elongated section overlaps the second elongated section a varying amount such that a length of the elongated body is adjustable.

24. The method of claim 21, wherein the first elongated section and the second elongated section are coaxially aligned.

25. The method of claim 21, wherein the biasing member comprises a rubber band configured to be positioned around the first hook and the second hook.

26. The method of claim 21, wherein one of the first elongated section and the second elongated section comprises a slot extending along at least a portion of its longitudinal length and a hook of the other of the first elongated section and the second elongated section extends through the slot and is configured to travel along the slot to adjust a length of the elongated body.

27. The method of claim 21, wherein connecting one of the selected pair of orthodontic appliances to the right side connector of the first removable orthodontic aligner and the right side connector of the second removable orthodontic aligner comprises connecting one of the selected pair of orthodontic appliances on a right side connector of the first removable orthodontic aligner located at a position corresponding to a first molar of the patient and a right side connector of the second removable orthodontic aligner located at a position corresponding to a second bicuspid of the patient.

* * * * *